United States Patent [19]
Beekman et al.

[11] Patent Number: 6,035,716
[45] Date of Patent: *Mar. 14, 2000

[54] METHOD AND DEVICE FOR CHARACTERIZING GRANULE STRENGTH

[75] Inventors: Willem Johan Beekman; Gabriel Marinus Henricus Meesters, both of Delft; Brian Scarlett, The Hague, all of Netherlands

[73] Assignee: Genencor International, Inc., Rochester, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/681,250

[22] Filed: Jul. 22, 1996

[51] Int. Cl.[7] .............................. G01H 1/00; G01G 3/16
[52] U.S. Cl. ............................................. 73/579; 73/580
[58] Field of Search ............................. 73/579, 580, 581, 73/582, 12.01, 808, 810

[56] References Cited

U.S. PATENT DOCUMENTS

| | | | |
|---|---|---|---|
| 3,282,084 | 11/1966 | Banks | 73/579 |
| 4,685,326 | 8/1987 | Peterson | 73/580 |
| 5,152,401 | 10/1992 | Affeldt, Jr. et al. | 73/279 |

FOREIGN PATENT DOCUMENTS 1213376  2/1986  Russian Federation ................. 73/579

*Primary Examiner*—Hezron Williams
*Assistant Examiner*—Helen C. Kwok
*Attorney, Agent, or Firm*—Nixon Peabody LLP

[57] ABSTRACT

The present invention provides a method and device for measuring granule impact strength by vibrating a small container of granules at a well-controlled amplitude in order to inflict reproducible damage to the granules. Damage to the granules is measured as a function of time and amplitude. The measurements characterize granule attrition and fragmentation.

15 Claims, 2 Drawing Sheets

METHOD AND DEVICE FOR CHARACTERIZING GRANULE STRENGTH

FIELD OF THE INVENTION

The present invention relates to a method and device for measuring the impact strength for individual granules over a wide distribution and for aspherical sizes.

BACKGROUND OF THE INVENTION

In any manufacturing involving the use or movement of particulate materials, some breakdown or attrition of the particles is inevitable and has been reported in a wide range of processes and industries. For example, it has significance for those applications where it is desirable for particles to remain in a process almost indefinitely. The effects of attrition can be loss of product by removal of undersize particles, the need for recycling lost product, and the requirement for additional filtration. Another effect can be to limit the useful life of catalyst or enzyme particles.

Many products in the pharmaceutical industry, for example, are agglomerated granules which can suffer attrition during processing and also, if bulk packed, during shipment and use. Dust release into the atmosphere may be a hazard, but its release is also undesirable because of the high value of many of the products.

Attrition has a number of different effects, the relative importance of which is dependent upon the commercial or technical application. Properties of particulate materials change as a result of attrition. Loss of material occurs due to the change of particle sizes to smaller ones which are unacceptable to the particular process and which are removed from the process by accident or design in cyclones, filters, or precipitators. Wear of contaminant systems results from the impact of particles with the walls of the container or duct, and contamination of the process particles by debris from wear of the containment system may be significant in some applications. Even an explosion can be caused if a build-up of fine material is allowed to occur.

Several conventional methods for testing the mechanical strength of industrial catalysts which are used in fluid beds are reported in C. R. Bemrose and J. Bridgwater, A Review of Attrition and Attrition Test Methods, *Powder Technology*, 49 (1987) 97–126. One of the vibration tests discussed therein used a container enclosing a granular charcoal bed which was vibrated at 60 Hz with an acceleration of 5 g. Air was blown into the top of the container and dust formed by the attrition of the granular charcoal passed through the perforated base of the container to be collected on a glass fiber filter paper. As a result, the impact strength of the entire bed was tested and not individual particles.

Another vibration test is reported in T. P. Ponomareva, S. I Kontorovich, and E. D. Shchukin, Attrition Of Spherical Cracking Catalysts in the Presence Of Powdered Lubricants, *Kinetics and Catalysis*, 21 (1980) 505–510 for measuring the wear between catalyst particles treated with a lubricant powder. The test used a specially constructed cylindrical drum undergoing vertical vibrational movement imposed by a vibro-saw at a frequency of 50 Hz and an amplitude of 6 mm. Only the amount of wear between the catalyst particles themselves could be measured by removing the abrasion products through sieves located in the drum.

These methods have proven unsuitable for characterizing the individual particle since these methods vibrate an entire bed within a closed vessel. They measure the particle to vessel-wall interaction when the attrition and fragmentation of the particles is primarily caused by the particles rubbing each other. The impact velocity of the collisions encountered by the particle bed is also poorly defined by these methods and may be inaccurate due to some collisions encountering drag forces within the bed. Furthermore, some of these methods only measure spherical particles and are poorly adapted to accurately characterize aspherical or non-uniform shaped particles.

Thus, a need exists for a method and device for assessing attrition and fragmentation characteristics of particles during handling. A tool is needed to help develop particles which are individually strong since the mechanical stability of the particle is of primary importance in many industrial fields such as enzyme formulation technology. Characterizing the impact strength of individual particles, as opposed to entire particle bed, provides information that can be used to develop particles with enhanced attrition strength.

SUMMARY OF THE INVENTION

The present invention provides a test device for characterizing the impact strength of a granule. The test device includes a first container having an interior cavity larger than the size of the granule and means for vibrating the first container in a generally unidirectional movement at a predetermined frequency of resonance with sufficient strength to provide reproducible damage to the granule, the vibrating means connected to the first container.

The present invention also provides a test device for characterizing the impact strength of a granule which includes a vibrator providing a generally unidirectional movement at a predetermined frequency and a first container having an interior cavity larger than the size of the granule. The device further includes a first spring configured to connect at one end to the vibrator. The opposite end of the first spring is configured to connect to the container. The first spring has a predetermined frequency of resonance adapted to amplify the frequency of the vibrator movement and impart the amplification to the container.

A method of characterizing the impact strength of a granule is also provided by the present invention. The method includes the steps of: vibrating a sealed container having an interior space for confining a plurality of granules at a predetermined resonant frequency for a predetermined period of time and amplitude; removing the damaged granules from the container; and measuring the amount of undamaged granules.

Accordingly, it is an object of the present invention to provide a method and device for characterizing the impact strength of an individual granule.

Another object of the present invention is to provide a method and device which is adaptable to characterizing aspherical or non-uniformly shaped granules and accurately relates single granule to multiple granule results.

It is a further object of the present invention to provide a device which provides a higher number of well-controlled impacts for each granule compared to the prior art.

Still another object of the present invention is to provide a test device which is inexpensive to build and operate for a large number of representative samples to yield reproducible test results easily obtained without extensive operator training.

A further object of the present invention is to provide a test device which provides granules with collision orientations which are equally likely and minimizes drag force.

Other and further advantages, embodiments, variations and the like will be apparent to those skilled-in-the-art from the present specification taken with the accompanying drawings and appended claims.

BRIEF DESCRIPTION OF THE DRAWINGS

In the drawings, which comprise a portion of this disclosure.

DESCRIPTION OF THE PREFERRED EMBODIMENTS

Figure 1:
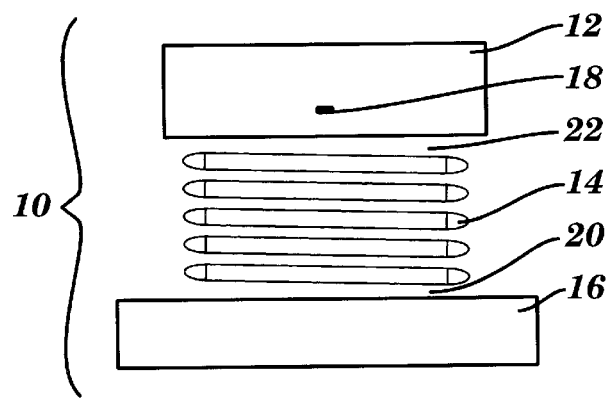
FIG. 1 is a side view of a schematic illustrating a test device for measuring the impact strength of a granule as provided by the present invention.

The present invention provides a method and device for measuring granule impact strength by vibrating a small container of one or more granules at a well-controlled amplitude in order to inflict reproducible damage to the granules. Damage to the granules is measured as a function of time and amplitude. The measurements obtained yield a highly reproducible means for characterizing granule attrition and fragmentation.

The term attrition as used herein includes the unwanted breakdown of particles within a process. Attrition includes both abrasion and fragmentation provided these are unwanted. Fragmentation is the process whereby a particle splits into smaller parts, usually large in number and including a range of sizes of particles produced by the breakage of larger particles. Abrasion is the removal of material from a particle such that the material removed is much smaller than the particle.

The term granule as used herein includes one or more particles or an agglomerate. An agglomerate is an assemblage of particles which are either loosely or rigidly joined together. A particle includes a piece of material which is an entity in itself. It may be porous or contain faults or cracks, but in general has not been formed by joining together two or more smaller pieces of material.

Damage to granules can be inflicted by creating a defined strain upon the granules through a number of different methods. For example, the direction of the strain of a compressive force with respect to the geometry of the granules can be changed. The geometry of the force can vary to exert either an impact, slow compressive, or very fast compressive force. The strain can be dependent on the shape and size of the granules.

As discussed above, one of the problems with using the current methods is receiving reproducible, and thus more useable, results. When inflicting damage towards a granule, it is difficult to inflict the damage in a reproducible way. Without a reproducible starting point, the results are spread over a wide range and are difficult to interpret. If this problem is overcome by reproducibly inflicting damage, the spread in the results are reduced significantly. The test results presented herein using the present invention will demonstrate a more reproducible method of inflicting damage and more meaningful results compared to the current methods.

Another problem with using these methods previously discussed is that only granules with well-controlled fabrication histories are well-suited for measurement. When a granule is deformed, inhomogeneities can concentrate local stresses and can seriously reduce granule strength. In general, the granule will be inhomogeneous, asymmetrical and aspherical. When a granule has been built up using layering techniques, the inhomogeneities which are accidental will be observed. The presence of cracks in the granules can be important for determining granule strength. The fabrication history of the granule such as the number of impacts, observed temperature or humidity gradients can affect the determination of granule strength. The present invention is not so limited and provides a reproducible measurement of the strength of the individual granule even though it is affected by the geometry of the strain, the velocity of the impact or strain, the direction of the force and the size and shape of the granules.

The present invention provides a test device 10 having a container 12 mounted on a spring 14 which, in turn, is mounted on a vibrator 16. The container 12 is preferably made of a light weight metal which is strong and seals dust-tight. A granule 18 is confined within the container 12 for testing. The height of the container 12 is much larger than the diameter of the granule 18 (preferably, in excess of about 50 times). Having the dimension of the container 12 in the direction of the container's travel so much larger, provides the granule 18 with free movement within the container for a longer period of time. High impact velocities result when the container 12 has more time to decelerate before impacting the granule 18 and creates a larger velocity difference between the wall of the container and the granule.

The container 12 vibrates with an amplitude which is larger than the height of the container 12 to assure that the granule 18 inside the container 12 is forced to bounce to the walls on both sides of the container 12. The amplitude of the vibration is proportional to the velocity of the container 12. Preferably, the granules are shaken with accelerations up to about 400 g at amplitudes from about 0.25 cm to about 4.0 cm.

The spring 14 is selected accordingly to have a predetermined frequency of resonance such as, for example and not limited to, about 50 Hz. The vibrator 16 shakes with a small amplitude at the selected resonance frequency which results in strongly amplifying the movement imparted to the container 12. For example, when the vibrator 16 shakes with an amplitude of only about 1 mm at one end 20 of the spring 14, the container 12 can easily reach amplitudes of about 50 mm at the other end 22 of the spring. Any conventional vibrator, preferably having a vertical motion, is suitable for use with the present invention. One example is a vibrating table.

The test device 10 provides a means to make the granules collide with the walls of the container 12 in a well-controlled manner. By adjusting the mass of the container 12 (adding or subtracting small amounts of mass), the total mass spring system can be fine tuned to yield a resonance frequency. Preferably, the resonance frequency of 50 Hz (European mains) is used.

In operation, the container 12 is subjected to several predetermined periods of vibration. The percentage of mass of undamaged granules is determined after each period of vibration. The damaged granules are removed from the container 12 by passing them through an appropriately sized sieve. Preferably, a sieve having a size of about 315 μm is used. Determining the number of undamaged granules still present yields the percentage of granules not fragmented. With this information, the development from attrition to fragmentation can be monitored.

Figure 2:
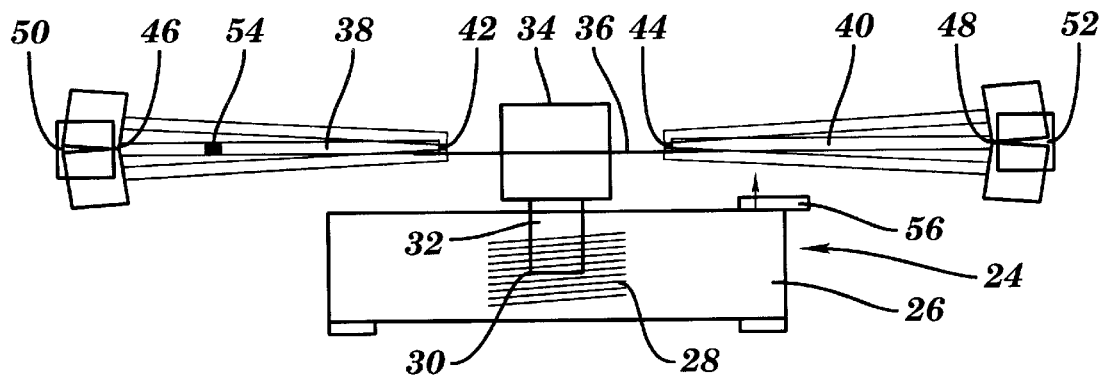
FIG. 2 is a side view of a preferred embodiment of a test device provided by the present invention with a portion of the device box cut-away to illustrate the internal spring mechanism.

A preferred embodiment of the inventive test device for dynamically testing the strength of a granule is illustrated in FIG. 2. The test device 24 includes a housing 26 for supporting a spring 28 therein. The spring 28 connects to one end 30 of a rod 32 extending externally from the housing 26. Connected to the opposite end 34 of the rod 32 is an elongated support which connects to a tempered blade spring 36. A pair of rigid arms 38, 40 connect at one end 42, 44 to opposite sides of the blade spring 36. The other ends 46, 48 of the rigid arms 38, 40 connect to a pair of containers 50, 52, respectively. Preferably, the arms 38, 40 are made of aluminum and are attached in a symmetrical arrangement centered on the blade spring 36 in order to avoid problems with impulse-momentum stability. A small weight 54 slidably attached along the longitudinal direction of one, or both, arms 38, 40 can be used to adjust the resonance frequency of the containers 50, 52.

Figure 3:
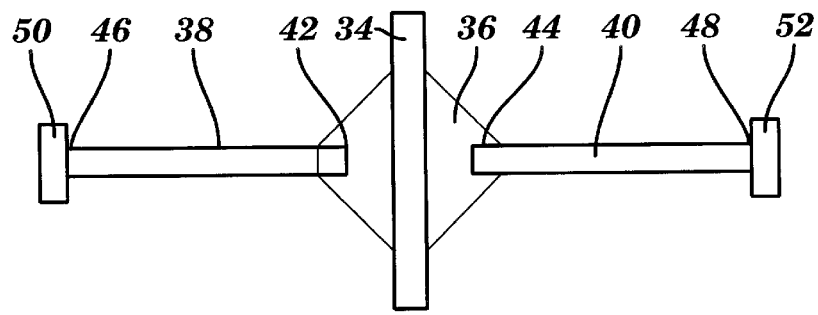
FIG. 3 is a top surface view of the device in FIG. 2 isolating the symmetrical blade spring, containers and vibrator.

FIG. 3 illustrates in greater detail the blade spring 36 rigidly connected to the end 34 of the rod along the elongated support. Since conventional wound springs are too heavy for reaching high resonance frequencies, the present invention adds a second spring means by utilizing the blade spring 36. The shape and material comprising the blade spring 36 allows flexing to occur between the ends 42, 44 of the rigid arms 38, 40 and the end of the rod 34. The flexing of the blade spring 36 allows the containers 50, 52 to reach a higher resonance frequency.

The amplitude achieved by the containers 50, 52 based on the concept of the resonating spring blade 36 is illustrated by the phantom images in FIG. 2. As the agitation is near to the resonance frequency of the mass spring combination, large amplitudes can be achieved. The frequency of operation is dictated by the mains which is preferably about 50 Hz. Therefore, the container travels a complete cycle about every 20 milliseconds (ms)

In operation, both containers 50 and 52 can be used for testing granules. It has been observed, however, that when the amplitude of one container of the test device 24 is declined, additional energy appears to be directed to the other container, yielding a higher amplitude. This provides the opportunity for a robust mechanical feedback for amplitude regulation when only one container of the test device 24 is used for granule testing. The amplitude of the container with the granule is simply restricted to a certain maximum. Enough energy is applied to the test device 24 so as to ensure a regulating effect of the mechanical feedback. All excess energy is then directed by the test device 24 to the container which is not being used to test the granule.

The amplitude can be controlled easily by installing a mechanical limit 56 to the allowed travel of the resonating system. An amplitude is set in the vibration test by adjusting the height of the mechanical limit 56.

Another preferred embodiment is useful when hardly any damage is found using the test devices described above. In this alternate embodiment, one or more metal balls are added to the container with the granules. For example, in measuring catalyst particles of 70 μm size, a single metal ball of 4 mg is added to the container. Any object having an impact strength significantly larger than the granule and a diameter less than the interior cavity of the container is suitable for use in the present invention. Damage is observed by sieving over 50 μm.

Due to the oscillating behavior of the container, the metal ball situated inside the container is forced into synchronized motion, bouncing from side to side every 20 ms. Damage occurs to granules also present in the container from collisions between the metal ball and the granules or from collisions between the granules and the container walls. With every cycle of the container several collisions are possible, although collisions cannot be guaranteed.

This mode of operation for the present invention differs from the collisions previously described directly between the granules and the walls of the container. It is guaranteed that in every cycle of the container, each granule collides with the container wall and in this way many random orientated collisions are obtained, all with a very defined impact velocity. As a result, all possible collision orientations will occur within a short time period.

Having generally described the present invention, a further understanding can be obtained by reference to the following specific examples, which are provided herein for purposes of illustration only and are not intended to be limiting of the present invention.

EXAMPLE 1

Figure 4:
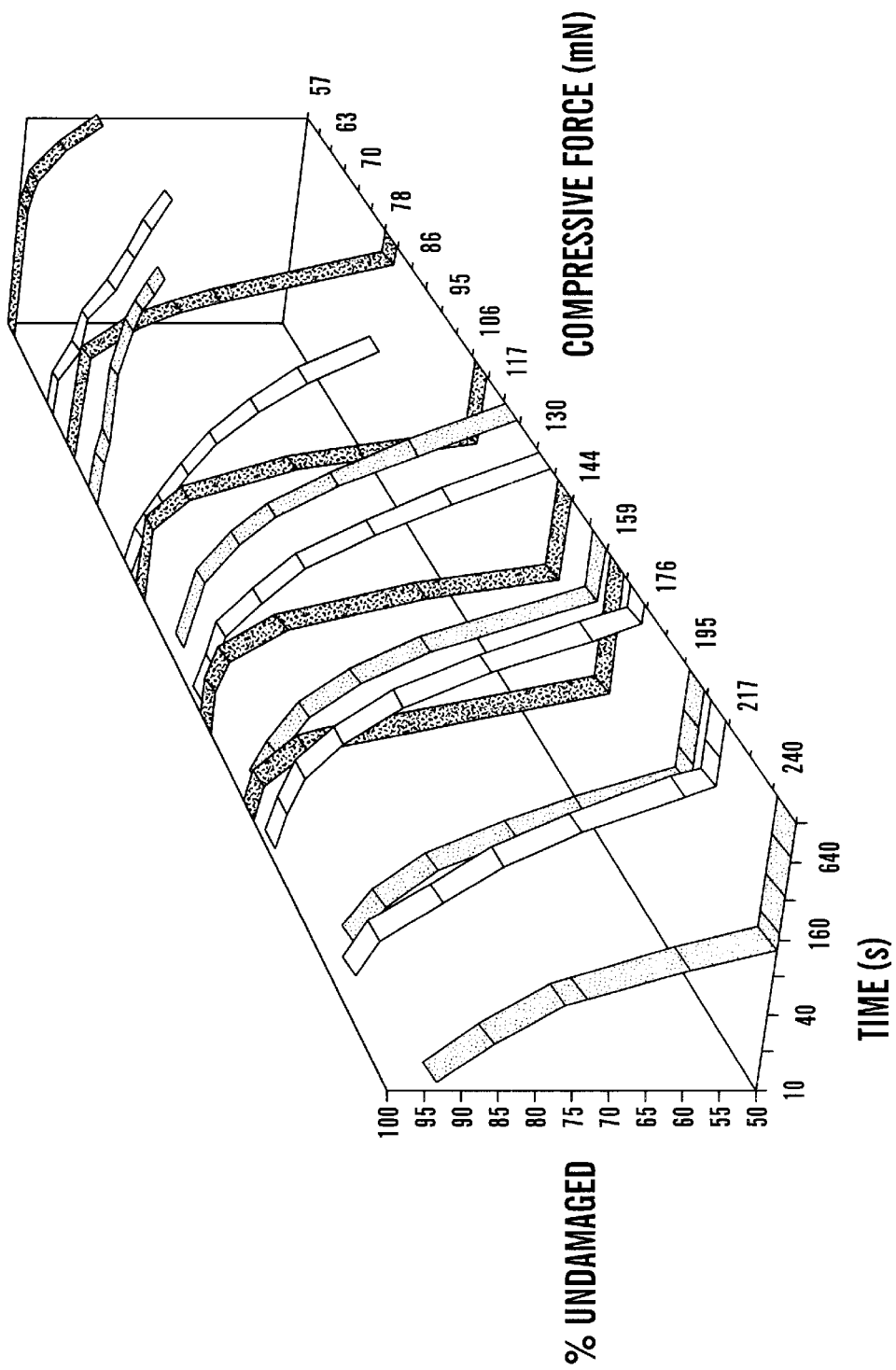
FIG. 4 is a graph of the percentage of undamaged particles versus time across a range of different compressive forces.

Unless otherwise stated, the following procedure was used in obtaining the test results presented in the tables and FIG. 4. Using the preferred embodiment test device 24, the amplitude was set in the vibration test by adjusting the height of the mechanical limit. The containers were made of plastic having a height of about 2.5 cm and were thoroughly cleaned. The preferred length of each rigid arm 38, 40 and container 50, 52 was about 15 cm. The amplitude of vibration was controlled in the preferred range of about 0.5 cm to about 2.0 cm.

About 30 mg of granules (which is about 150 pieces) having a size range of about 0.4 mm to about 1.0 mm were put into one of the plastic containers. The container was sealed dust tight with adhesive tape. The container was shaken during an interval of time into its resonance frequency (for example 10s, 20s, 40s and 80s). After each period of time, the contents of the container were sieved using a 315 μm sieve to remove the damaged granules.

By taking pictures of the undamaged fraction, it was possible to determine the proportion of attrition versus fragmentation. The percentage of mass that was unbroken was determined and this fraction was put back into the container. The container was sealed and shaken for another interval of time.

This was repeated for a number (n=5) of different amplitudes by adjusting the mechanical limit. A three dimensional picture was formed by plotting either attrition or breakage as a function of velocity and the number of repetitions.

The test device was first used to demonstrate that the results were not influenced by the number of granules tested at one time. Table 1 reports the results from using enzymes containing layered granules.

TABLE 1

| | Layered Granules | | |
|---|---|---|---|
| Time (s) | m = mass [mg] m retained | n = number of granules n = 10 [%] | n = number of granules n = 309 [%] |
| 0 | 1.36 | 100 | |
| 20 | 1.07 | 79 | |
| 60 | 0.86 | 63 | |

TABLE 1-continued

| | Layered Granules | | |
|---|---|---|---|
| Time (s) | m = mass [mg] m retained | n = number of granules n = 10 [%] | n = number of granules n = 309 [%] |
| 80 | 0.68 | 50 | |
| 160 | 0.23 | 17 | |
| 320 | 0.21 | 15 | |
| 0 | 41.99 | | 100 |
| 10 | 41.44 | | 99 |
| 20 | 39.87 | | 95 |
| 40 | 34.14 | | 81 |
| 80 | 23.68 | | 56 |
| 160 | 11.22 | | 27 |
| 320 | 6.14 | | 15 |

One of the advantages of running tests on a larger number of granules is to reduce the difference between samples and the inaccuracy of determining the granules' weight. Furthermore, fragmentation is a discrete effect, so large numbers of granules are required for obtaining smooth, more meaningful signals. A suitable method of damage assessment for larger samples is to sieve over half the original granule size e.g. 310 $\mu$m when granules of about 600 $\mu$m are used. It appears that smaller sieves can be used as well, as granule fragments are quickly reduced to a small size.

EXAMPLE 2

A series of tests was carried out with three commercial available granules: Genencor CXT 600.000 prills (Prills), Genencor Fluid Bed Granules (FBG) from Genencor and Savinase 4.0T from NOVO Nordisk (Enzyme Layered Granules-(ELG) ). Results are listed in Tables 2, 3, and 4. It was observed that the results appear independent from the amount of granules in the test within the range identified in the above Example. The spread in the results appears to be very low (on average less than 2% for 25% of damage).

About 30 mg of each commercially available granule product was introduced into the test and vibrated with different amplitudes of the container for several time intervals. After each period the amount of undamaged granules was determined by sieving the granules over 315 $\mu$m.

Table 2 gives the results for granule product ELG. Observing the results across the columns, the effect of increasing the amplitude [A] of the container can be monitored. Average particle size in the tests was between 590 and 710 $\mu$m, average granule mass was determined from counting the number of granules introduced to the test: 0.29 mg.

TABLE 2

| | ELG Undamaged [m %] | | | | |
|---|---|---|---|---|---|
| ELG | A [cm] | | | | |
| time [s] | 2 | 1.7 | 1.3 | 1 | 0.7 |
| 10 | 93 | 95 | 97 | 98 | 100 |
| 20 | 86 | 91 | 95 | 97 | 100 |
| 40 | 77 | 84 | 91 | 96 | 99 |
| 80 | 61 | 73 | 84 | 92 | 99 |
| 160 | 41 | 58 | 74 | 86 | 99 |
| 320 | 21 | 39 | 58 | 77 | 98 |
| 640 | 7 | 17 | 40 | 65 | 96 |
| 1280 | 3 | 7 | 24 | 51 | 93 |

EXAMPLE 3

Table 3 gives the results for granule product Prill. Again, about 30 mg of product was introduced into the test and vibrated with different amplitudes for several time intervals. After each period the amount of undamaged granules was determined by sieving over 315 $\mu$m. The average granule size was between 590 and 710 $\mu$m, average granule mass was determined from counting the number of granules introduced to the test: 0.17 mg.

TABLE 3

| | Prill undamaged [m %] | | | | |
|---|---|---|---|---|---|
| Prill times | A [cm] | | | | |
| [s] | 2 | 1.7 | 1.3 | 1 | 0.7 |
| 10 | 97 | 99 | 99 | 100 | 100 |
| 20 | 94 | 98 | 98 | 99 | 100 |
| 40 | 86 | 96 | 97 | 96 | 97 |
| 80 | 78 | 91 | 92 | 93 | 96 |
| 160 | 68 | 83 | 86 | 89 | 92 |
| 320 | 54 | 71 | 76 | 83 | 89 |
| 640 | 38 | 57 | 65 | 76 | 87 |
| 1280 | 15 | 40 | 51 | 65 | 84 |

EXAMPLE 4

Table 4 gives the results for the granule product FBG. About 30 mg of product was introduced into the test and vibrated with different amplitudes for several time intervals. After each period, the amount of undamaged granules was determined by sieving over 310 $\mu$m. Average particle size in the experiments was between 590 and 710 $\mu$m, average particle mass was determined from counting the number of granules introduced to the test: 0.16 mg.

TABLE 4

| | FBG Undamaged [m %] | | | | |
|---|---|---|---|---|---|
| FBG | A [cm] | | | | |
| time [s] | 2 | 1.7 | 1.3 | 1 | 0.7 |
| 10 | 100 | 100 | 100 | 100 | 100 |
| 20 | 99 | 100 | 100 | 100 | 100 |
| 40 | 92 | 99 | 100 | 100 | 100 |
| 80 | 68 | 91 | 95 | 100 | 100 |
| 160 | 40 | 70 | 79 | 94 | 100 |
| 320 | 22 | 37 | 51 | 80 | 99 |
| 640 | 11 | 16 | 26 | 58 | 95 |
| 1280 | 5 | 9 | 15 | 40 | 88 |

The results measured by the present invention and reported in Tables 2, 3, and 4 provide information not easily made available by the current methods. The results across the rows of the Tables identify the cumulative strength distribution of the granules as a function of their fatigue history. The results across the columns of the Tables identify the development of the percentage undamaged as a function of fatigue.

One interpretation provided by each of the Tables is a comprehensive description of the strength behavior of the granule during dynamic processes such as pneumatic transport and dosing. During pneumatic transport, granules suffer from collisions with the wall in a comparable way as the collisions generated in the tests of the present invention. Thus, the tests provide an indication of the damage occurring to the granules during transport.

Using constant velocities as the criterion, tests at constant amplitude should be compared.

Another interpretation provided by each of the Tables is the fatigue caused by dynamic and static compressive forces.

Since amplitude is easily varied and the number of collisions is controlled by the duration of each test, a complete characterization is available for granule fatigue as a function of velocity of impact. As for low velocity impacts (about 10 m/s) most deformation of the granules is primarily elastic. One can convert velocity of impact to compressive force of impact when the compressibility constant is known.

With this information, different types of granules can be compared by their fatigue results. Effects of differing mass can be incorporated if, as a first approximation, elastic collisions are assumed: $0.5 \, mv^2 = 0.5 \, F_{max}^2/S$, where S is granule stiffness and the maximum occurred compressive force. Thus, $F_{max} = v\sqrt{(mS)}$. Granule stiffness as used herein is the initial linear relation between granule deformation and required compressive force. Table 5 presents the mean result of measurements of granule stiffness for the three commercial granule products tested herein which allows calculation of the compressive forces in the impact tests.

TABLE 5

|  | Stiffness [N/mm] |
| --- | --- |
| ELG | 10.6 |
| Prill | 14.6 |
| FBG | 13 |

Using the formula for $F_{max}$, the maximum compression force during impact can be calculated and the influence of mass of granules during impact can be incorporated. The calculated forces using container velocities, average mass and granule stiffness, for each commercial granule product tested herein is presented in Table 6.

TABLE 6

| A [cm] | ELG v [m/s] | F [N] | FBG v [m/s] | F [N] | Prill v [m/s] | F [N] |
| --- | --- | --- | --- | --- | --- | --- |
| 2.0 | 3.9 | 0.24 | 3.9 | 0.16 | 3.9 | 0.19 |
| 1.7 | 3.2 | 0.2 | 3.2 | 0.14 | 3.2 | 0.17 |
| 1.3 | 2.6 | 0.16 | 2.6 | 0.1 | 2.6 | 0.13 |
| 1.0 | 2.0 | 0.12 | 2.0 | 0.08 | 2.0 | 0.10 |
| 0.7 | 1.3 | 0.08 | 1.3 | 0.06 | 1.3 | 0.07 |

The tests performed by the present invention are extremely well-defined in terms of impact velocity, impact orientation, impact force and history of the granules. Therefore, it is an extremely well-defined test for granule fatigue. Plotting the results as a function of fatigue presents a very clear picture of particle strength which can not be readily obtained using the prior art methods.

In FIG. 4, the results for the three different types of granule products are given as a function of fatigue parameters (force of fatigue and duration). The fatigue force has been calculated as described earlier. Clearly, results for a single type of granule are strongly related and appear to create three dimensional curved surfaces: the spacing of the fatigue surfaces from different granule types is a measure for granule strength.

Results of experiments with different sizes and different velocities for a single type of granule all lie on a well defined three dimensional curved surface. The curved surfaces illustrate that the use of compressive force and number of repetitions is a complete measure for granule fatigue. The surfaces provide a lot of information about fatigue development in the granules.

The complex analysis provided by the present invention is needed to accurately describe the damage to the three different types of granules in using compressive strength behavior.

As demonstrated by the results presented herein, the present invention can be used for characterizing, for example and not for limitation, granulated industrial catalysts, industrial enzymes, and food enzymes. The present invention is also applicable for identifying problems and providing solutions to the use of granules in the pharmaceutical industry, the grinding of clinker in the cement industry, the creation of dust in the milling of flour and other foodstuffs, or dust generated by mining and quarrying. Another example of the present invention's applicability is with the large particle attrition which occurs with railroad ballast where properties degrade due to the motion of the sleepers causing lateral instability. A further type of granule are strongly related and appear to create three dimensional curved surfaces: the spacing of the fatigue surfaces from different granule types is a measure for granule strength.

Results of experiments with different sizes and different velocities for a single type of granule all lie on a well defined three dimensional curved surface. The curved surfaces illustrate that the use of compressive force and number of repetitions is a complete measure for granule fatigue. The surfaces provide a lot of information about fatigue development in the granules.

The complex analysis provided by the present invention is needed to accurately describe the damage to the three different types of granules in using compressive strength behavior.

As demonstrated by the results presented herein, the present invention can be used for characterizing, for example and not for limitation, granulated industrial catalysts, industrial enzymes, and food enzymes. The present invention is also applicable for identifying problems and providing solutions to the use of granules in the pharmaceutical industry, the grinding of clinker in the cement industry, the creation of dust in the milling of flour and other foodstuffs, or dust generated by mining and quarrying. Another example of the present invention's applicability is with the large particle attrition which occurs with railroad ballast where properties degrade due to the motion of the sleepers causing lateral instability. A further application of the present invention is the generation of fines within packed columns used in gas-liquid chromatography which lowers efficiency and increases pressure drop.

Numerous modifications and variations of the present invention are possible in light of the above teachings. It is therefore to be understood that within the scope of the appended claims, the invention may be practiced otherwise than as specifically described herein.

What is claimed is:

1. A testing system for characterizing the impact strength of a granule, the testing system comprising:

a first container having an interior cavity larger than the size of the granule;

a vibrating assembly which vibrates the first container in a generally unidirectional movement at a predetermined frequency of resonance with sufficient strength to provide reproducible damage to the granule, the vibrating assembly connected to the first container; and an object for placing inside the first container, the object having an impact strength significantly greater than the granule and a diameter smaller than the interior cavity of the first container.

2. The system of claim 1 wherein the vibrating assembly includes means for amplifying a lower frequency to achieve the predetermined frequency of resonance, the amplifying means connected to the vibrating means.

3. The system of claim 1 wherein the device includes means for controlling a maximum and a minimum amplitude of the container from a resting position.

4. The system of claim 1 wherein the device further includes means for adjusting the predetermined frequency of resonance.

5. The system of claim 1 wherein the device includes a second container, the second container connected to the vibrating assembly, and the vibrating assembly includes means for amplifying a lower frequency to achieve the predetermined frequency of resonance, the amplifying means positioned between the vibrating assembly and the first and second containers.

6. A test device comprising:

a first container having an interior cavity larger than the size of a granule;

means for vibrating the first container in a generally unidirectional movement at a predetermined frequency of resonance with sufficient strength to provide reproducible damage to the granule, the vibrating means connected to the first container; and an object for placing inside the container, the object having an impact strength significantly greater than the granule and a diameter smaller than the interior cavity of the first container.

7. A test device comprising:

a vibrator providing a generally unidirectional movement at a predetermined frequency;

a first container having an interior cavity larger than the size of the granule;

a first spring connected at one end to the vibrator, the first spring having a predetermined frequency of resonance adapted to amplify the frequency of the vibrator movement and impart the amplification of the frequency of the vibrator movement to the container; and a spring assembly having a higher predetermined frequency of resonance than the first spring, the spring assembly connected between an opposite end of the first spring and the container.

8. The device of claim 7 wherein the force applied to the container is about 400 g or less.

9. The device of claim 7 wherein the range of amplitude for the container is about 0.5 cm to about 2.0 cm.

10. The device of claim 7 wherein the predetermined frequency of resonance of the spring is about 50 Hz.

11. A testing device for at least one granule, the testing device comprising:

a vibrator providing a generally unidirectional movement at a predetermined frequency:

a first container having an interior cavity larger than the size of the granule; and a first spring configured to connect at one end to the vibrator, the opposite end of the first spring configured to connect to the container, the first spring having a predetermined frequency of resonance adapted to amplify the frequency of the vibrator movement and impart movement to the container; and a spring assembly having a higher predetermined frequency of resonance than the first spring, the spring assembly configured to connect between the first spring and the container; and a second container, wherein the spring assembly further comprises:

an elongated rod, one end of the rod connecting to the end of the first spring opposite the vibrator;

a pair of arms; and a second spring, one end of the second spring connecting to the opposite end of the rod, the opposite end of the second spring connecting to one end of each of the arms, the opposite end of each of the arms connecting to one of the containers, the arms extending outwardly from the second spring in a symmetrical pattern.

12. The device of claim 11 wherein the device includes a mechanical limiter configured to control the amplitude of the container, the mechanical limiter positioned to intermittently engage and restrict the travel of one of the arms.

13. The device of claim 11 wherein the device includes a weight adjustably attached to one of the arms, the weight configured to adjust the frequency of resonance.

14. A test device comprising:

a vibrator providing a generally unidirectional movement at a predetermined frequency;

a first container having an interior cavity larger than the size of a granule;

a first spring configured to connect at one end to the vibrator, the opposite end of the first spring configured to connect to the container, the first spring having a predetermined frequency of resonance adapted to amplify the frequency of the vibrator movement and impart the amplification to the container; and an object for placing inside the container, the object having an impact strength significantly greater than the granule and a diameter smaller than the interior cavity of the first container.

15. The device of claim 7 further comprising a second container, wherein the spring assembly further comprises:

an elongated rod, one end of the rod connecting to the end of the first spring opposite the vibrator;

a pair of arms; and a second spring, one end of the second spring connecting to the opposite end of the rod, the opposite end of the second spring connecting to one end of each of the arms, the opposite end of each of the arms connecting to one of the containers.

* * * * *